United States Patent [19]

Smirnov et al.

[11] Patent Number: 5,837,843
[45] Date of Patent: Nov. 17, 1998

[54] MODIFIED PROTEIN C

[75] Inventors: Mikhail D. Smirnov; Charles T. Esmon, both of Oklahoma City, Okla.

[73] Assignee: Oklahoma Medical Research Foundation, Oklahoma City, Okla.

[21] Appl. No.: 745,254

[22] Filed: Nov. 8, 1996

[51] Int. Cl.$^6$ .................................................. C07H 21/04
[52] U.S. Cl. ..................... 536/23.5; 536/23.1; 530/381; 530/384; 435/91.1
[58] Field of Search ............................... 536/23.1, 23.5; 530/381, 384; 435/91.1

[56] References Cited

U.S. PATENT DOCUMENTS

| | | | |
|---|---|---|---|
| 4,968,626 | 11/1990 | Foster et al. | 435/320 |
| 5,009,889 | 4/1991 | Taylor, Jr. et al. | 424/94.64 |
| 5,225,537 | 7/1993 | Foster | 530/380 |

OTHER PUBLICATIONS

Gene et al. (1995) Biochemistry, vol. 34, pp. 8449–8457, 1995.
Yu et al. (1994) Biochemistry, vol. 33, pp. 823–831, 1994.
Zhong et al. (1993) Biotechniques, vol. 15, No. 5, pp. 874–878, 1993.
Friezner et al. (1987) Biochemistry, vol. 26, pp. 6165–6177, 1987.
Geng et al. (Aug. 26, 1996) Thrombosis and Haemostasis, vol. 76, No. 2, pp. 205–207, 1996.
Armstrong, et al., "The Active Site of Membrane–bound Meizothrombin," *J. Biol. Chem.* 265(11):6210–6218 (1990).
Bertina, et al., "Mutation in blood coagulation factor V associated with resistance to activated protein C" *Nature* 369(6475):64–67 (1994).
Bevers, et al., "Changes in Membrane Phospholipid Distribution During Platelet Activation," *Biochem. Biophys. Acta* 736:57–66 (1993).
Billy, et al., "Prothrombin Contributes to the Assembly of the Factor Va–Factor Xa Complex at Phosphatidylserine–containing Phospholipid Membranes," *J. Biol. Chem.* 270(45):26883–26889 (1995).
Bock*, "Active Site Selective Labeling of Serine Proteases with Spectroscopic Probes Using Thioester Peptide Cholromethyl Ketones Demonstration of Thrombin Labeling Using N$^\alpha$[(Acetylthio)acetyl]–D–PhePro–Arg–CH$_2$Cl†," *Biochemistry* 27:6633–6639 (1988).
Castellino F.J., "Human Protein C and Activated Protein C. Components of the Human Anticoagulation System," *Trends Cardiovasc. Med.*, 5(2):55–62 (1995).
Conway, et al., "Tumor Necrosis Factor Suppresses Transcription of the Thrombomodulin Gene in Endothelial Cells," *Mol. Cell. Biol.* 8(12):5588–5592 (1988).
D'angelo, et al., "Acquired Deficiencies of Protein S. Protein S Activity During Oral Anticoagulation, in Liver Disease, and in Disseminated Intravascular Coagulation," *J. Clin. Invest.* 81:1445–1454 (1988).
Dahlbäck, "Protein S and C4b–Binding Protein: Components Involved in the Regulation of the Protein C Anticoagulant System," *Thromb. Haemostas.* 66(1):49–61 (1991).
Dahbäck, "Inhibition of Protein $C_a$ Cofactor Function of Human and Bovine Protein S by C4b–binding Protein," *J. Biol. Chem.* 261(26):12022–12027 (1986).
Dahlbäck, "Inherited thrombophilia: resistance to activated protein C as a pathogenic factor of venous thromboembolism" *Blood* 85(3):607–614 (1995).
Devaux, "Static and Dynamic Lipid Asymmetry in Cell Membranes," *Biochemistry* 30(5): 1163–1173 (1991).
Dittman, "Thrombomodulin, Biology and Protein Cardiovascular Applications," *Trends Cardiovasc. Med.* 1(8):331–336 (1991).
Dittman, et al., "Review Article—Structure and Function of Thrombomodulin: A Natural Anticoagulant," *Blood* 75(2):329–336 (1990).
Dreyfus, et al., "Treatment of Homozygous Protein C Deficiency and Neonatal Purpura Fulminans with a Purified Protein C Concentrate," *N. Engl. J. Med.* 325(22):1565–1568 (1991).
Esmon, "The Function of Factor V In P rothrombin Activation," (Ph.D. Dissertation), Washington University, St. Louis (Dec., 1973).
Esmon, "The Roles of Protein C and Thrombomodulin in the Regulation of Blood Coagulation," *J. Biol. Chem.* 264(9):4743–4746 (1989).
Esmon, et al., "Protein C Activation," *Methods. Enzymology* 222:359–385 (Academic Press, Inc. 1993).
Esmon, "Protein S and Protein C—Biochemistry, Physiology, and Clinical Manifestation of Deficiencies," *Trends Cardiovasc. Med.* 2(6):214–220 (1992).
Esmon, "The Subunit Structure of Thrombin–activated Factor V," *J. Biol. chem.* 254(3): 964–973 (1979).
Florell, et al., "Inherited thrombotic disorders: An Update" *Am. J. Hematol.* 54(1):53–60 (1997).
Friezner, et al., "Nucleotide Sequence of the Gene for Human Prothrombin," *Biochemistry*, 26(18):6165–6177 (1987).
Furie, et al., "Molecular Basis of Blood Coagulation," *Cell* 53:505–518 (1988).
Geng, et al., "The Propeptides of Human Protein C, Factor VII, and Factor IX Are Exchangeable with Regard to Directing Gamma–Carboxylation of these Proteins," *Thrombosis and Haemostasis*, 76(2):205–207 (1996).

Primary Examiner—Rebecca E. Prouty
Assistant Examiner—Enrique D. Longton
Attorney, Agent, or Firm—Arnall Golden & Gregory, LLP

[57] ABSTRACT

Modified Protein C molecules have been made which substitute the gamma carboxylglutamic acid (Gla) region of another Vitamin K dependent protein, most preferably prothrombin, for the native region of the Protein C. The modified or chimeric protein C has advantages over the wild-type protein C since it is less sensitive to inhibition by natural inhibitors of protein C (which would otherwise decrease the ability of the protein C to act as an anticoagulant) and which does not need the same cofactors or same amounts of cofactors, and can therefore be effective in patients with lowered levels of the cofactors such as protein S or the lipids present in activated platelets such as phosphatidyl ethanolamine (PE).

7 Claims, 3 Drawing Sheets

OTHER PUBLICATIONS

Geng, et al., "Transfer of Specific Endothelial Cell–Binding Properties from the Procoagulant Protein Human Factor IX into the Anticoagulant Protein Human Protein C," *Biochemistry*, 34:8449–8457 (1995).

Gerson, et al., "Severe Acquired Protein C Deficiency in Purpura Fulminans Associated with Disseminated Intravascular Coagluation Treatment with Protein C Concentrate," *Pediatrics* 91(2)L418–422 (1993).

Gilbert, et al., "Phosphatidylethanolamine Induces High Affinity Binding Sites for Factor VIII on Membranes Containing Phosphatidyl–L–serine," *J. Biol. Chem.* 270(31):18500–18505 (1995).

Ginsberg, et al., "Increased Thrombin Generation and Activity in Patients with Systemic Lupus Erythematosus and Anticardiolipin Antibodies: Evidence for a Prothrombotic State," *Blood* 81(11):2958–2963 (1993).

Heeb, et al., "Binding of Protein S to Factor Va Associated with Inhibition of Prothrombinase That is Independent of Activated Protein," *J. Biol. Chem.* 268(4):2872–2877 (1993).

Kalafatis, et al., "Characterization of the molecular defect in factor $V^{R506Q}$," *J. Biol. Chem.* 270(8):4053–4057 (1995).

Kalafatis, et al., "The mechanism of inactivation of human factor V and human factor Va by activated protein C" *J. Biol. Chem.* 269(50):31869–31880 (1994).

Le Bonniec, et al., "The Role of Calcium Ions in Factor X Activation by Thrombin E192Q", *J. Biol. Chem.* 267(10):6970–6976 (1992).

Lentz, et al., "Regulation of Thrombomodulin by Tumor Necrosis–α: Comparison of Transcriptional and Posttranscriptional Mechanism," *Blood* 77(3):543–550 (1991).

Mann, et al., "Cofactor Proteins in the Assembly and Expression of Blood Clotting Enzyme Complexes," *Ann. Rev. Biochem.* 57:915–956 (1988).

Mann, et al., "Surface Dependent Hemostasis," *Sem. Hematol.* 29(3):213–226 (1992).

Moore, et.al., "Tumor Necrosis Factor Leads to the Internalization and Degradation of Thrombomodulin From the Surface of Bovine Aortic Endothelial Cells in Culture," *blood* 73(1)159–165 (1989).

Nelsestuen, "Interaction of Vitamin K Dependent Proteins with Membranes," *Biochemistry* 17(11):2134–2138 (1978).

Neuenschwander, et al., "Phosphatidylethanolamine Augments Factor VIIa–Tissue Factor Activity: Enhancement of Sensitivity to Phosphatidylserine," *Biochemistry* 34(43): 13988–13993 (1995).

Owen, et al., "The Conversion of Prothrombin to Thrombin," *J. Biol. Chem.* 249(2):594–605 (1974).

Pei, et al., "Specific Contribution of Different Phospholipid Surfaces to the Activation of Prothrombin by the Fully Assembled Protrombinase," *J. Biol. Chem.* 268(5):3226–3233 (1992).

Pierangeli, et al., "Effect of Human IgG Antiphospholipid Antibodies on an In Vivo Thrombosis Model in Mice," *Thromb. Hæmostas.* 71(5):670–674 (1994).

Rauch, et al., "Human Hybridoma Lupus Anticoagulants Distinguish Between Lamellar and Hexagonal Phase Lipid Systems," *J. Biol. Chem.* 261(21):9672–9677 (1986).

Rezaie, et al., "The Function of Calcium in Protein C Activation by Thrombin and the Thrombin–Thrombomodulim Complex Can Be Distinguished by Mutational Analysis of Protein C Derivatives," *J. Biol. Chem.* 267(36):26104–26109 (1992).

Rezaie, et al., "Conversion of Glutamic Acid 192 to Glutamine in Activated Protein C Changes to Subtrate Specificity and Increases Reactivity Toward Macromolecular Inhibitors," *J. Biol. Chem.* 268(27). 19943–19948 (1993).

Seligsohn, et al., "Homozygous Protein C Deficiency Manifested by Massive Venous Thrombosis in the Newborn," *N. Eng. J. Med.* 310(9):559–562 (1984).

Smeets, et al., "Contribution of Different Phospholipid Classes to the Prothrombin Converting Capacity of Sonicated Lipid Visicles," *Thromb. Res.* 81(4):419–426 (1996).

Smirnov, et al., "On the Role of Phosphatidylethanolamine in the Inhibition of Activated Protein C Activity by Antiphospholipid Antibodies," *J. Clin. Invest.* 95:309–316 (1995).

Smirnov, et al., "Phosphatidylethanolamine Incorporation into Vesicles Selectivley Enhancers Factor Va Inactivation by Activated Protein C," *J. Biol. Chem.* 269(2):816–819 (1993).

Solymoss, et al., "Kinetics of Inactivation of Membrane–bound Factor Va by Activated Protein C," *J. Biol. Chem.* 263(29):14884–14890 (1988).

Taylor, et al., "Protein C Prevents the Coagulopathic and Lethal Effects of *Escherica coli* Infusion in the Baboon," *J. Clin. Invest.* 79:918–925 (1987).

Taylor, et al., "C4b–Binding Protein Exacerbates the Host Response to *Escherichia coli*," *Blood* 78(2):357–363 (1991).

Triplett, "Antiphospholipid Antibodies and Thrombosis," *Arch. Pathol. Lab. Med.* 117:78–88 (1993).

Wang, et al., "Estimation of the Phospholipid Distribution in the Human Platelet Plasma Membrane Based on the Effect of Phospholipase $A_2$ from *Naja nigricollis*," *Biochem. Biophys. Acta* 856:244–258 (1986).

Yu, et al., "Construction, Expression, and Properties of a Recombinant Chimeric Human Protein C with Replacement of Its Growth Factor–like Doamins by Those of Human Coagulation Factor IX," *Biochemistry* 33:823–831 (1994).

Zhang, et al., "The Contribution of Individual Y–Carboxyglutamic Acid Residues in the Calcium–dependent Binding of Recombinant Human Protein C to Acidic Phospholipid Vesicles," *J. Biol. Chem.* 268(16):12040–12045 (1993).

Zhong, et al., "A PCR–Base Method for Site–Specific Domain Replacement That Does Not Require Restriction Recognition Sequences," *Biotechniques*, 15(5):874–878 (1993).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 42 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY:
( B ) LOCATION: 6, 7, 14, 16, 19, 20, 25, 26, 29, 32
( D ) OTHER INFORMATION: /note= "where Xaa means gamma carboxylglutamic acid"

( i x ) FEATURE:
( A ) NAME/KEY:
( B ) LOCATION:
( D ) OTHER INFORMATION: /note= "partial sequence of human prothrombin"

( x i ) SEQUENCE DESCRIPTION: SEQ ID NO:1:

```
Ala Asn Thr Phe Leu Xaa Xaa Val Arg Lys Gly Asn Leu Xaa Arg Xaa
1               5                   10                  15
Cys Val Xaa Xaa Thr Cys Ser Tyr Xaa Xaa Ala Phe Xaa Ala Leu Xaa
            20                  25                  30
Ser Ser Thr Ala Thr Asp Val Phe Trp Ala
        35                  40
```

( 2 ) INFORMATION FOR SEQ ID NO:2:

( i ) SEQUENCE CHARACTERISTICS:
( A ) LENGTH: 42 amino acids
( B ) TYPE: amino acid (C) STRANDEDNESS: single
        (D) TOPOLOGY: linear (i i) MOLECULE TYPE: peptide (i x) FEATURE:
        (A) NAME/KEY:
        (B) LOCATION: 6, 7, 14, 16, 19, 20, 25, 26, 29
        (D) OTHER INFORMATION: /note= "where Xaa means gamma (i x) FEATURE:
        (A) NAME/KEY:
        (B) LOCATION:
        (D) OTHER INFORMATION: /note= "partial sequence of human
            protein C"

(x i) SEQUENCE DESCRIPTION: SEQ ID NO:2:

Ala  Asn  Ser  Phe  Leu  Xaa  Xaa  Leu  Arg  His  Ser  Ser  Leu  Xaa  Arg  Xaa
1              5                        10                       15

Cys  Ile  Xaa  Xaa  Ile  Cys  Asp  Phe  Xaa  Xaa  Ala  Lys  Xaa  Ile  Phe  Gln
              20                        25                       30

Asn  Val  Asp  Asp  Thr  Leu  Ala  Phe  Trp  Ser
              35                   40

(2) INFORMATION FOR SEQ ID NO:3:

(i) SEQUENCE CHARACTERISTICS:
        (A) LENGTH: 32 nucleic acids
        (B) TYPE: nucleic acid
        (C) STRANDEDNESS: single
        (D) TOPOLOGY: linear (i i) MOLECULE TYPE: synthetic DNA (i x) FEATURE:
        (A) NAME/KEY:
        (B) LOCATION:
        (D) OTHER INFORMATION: /note= "forward prothrombin sense
            primer"

(x i) SEQUENCE DESCRIPTION: SEQ ID NO:3:

CGCTAAGCTT  CCATGGCCCG  CATCCGAGGC  TT                                        32

(2) INFORMATION FOR SEQ ID NO:4:

(i) SEQUENCE CHARACTERISTICS:
        (A) LENGTH: 34 nucleic acids
        (B) TYPE: nucleic acid
        (C) STRANDEDNESS: single
        (D) TOPOLOGY: linear (i i) MOLECULE TYPE: synthetic DNA (i x) FEATURE:
        (A) NAME/KEY:
        (B) LOCATION:
        (D) OTHER INFORMATION: /note= "reverse prothrombin antisense
            primer"

(x i) SEQUENCE DESCRIPTION: SEQ ID NO:4:

GAGTGGTCAC  CGTCTGTGTA  CTTGGCCCAG  AACA                                      34

MODIFIED PROTEIN C

The United States government has certain rights in this invention by virtue of grant No. P50 54502 awarded by the National Heart, Lung and Blood Institute of the National Institutes of Health to Naomi Esmon.

BACKGROUND OF THE INVENTION

The present invention is generally in the area of a modified protein C having enhanced anticoagulant activity.

Protein C plays a major role in the regulation of blood coagulation. Patients deficient in protein C usually exhibit life threatening thrombotic-complications in infancy (Seligsohn et al., (1984) *N. Engl. J. Med.* 310, 559–562; Esmon, (1992) *Trends Cardiovasc. Med.* 2, 214–220) that are corrected by protein C administration (Dreyfus et al., (1991) *N. Engl. J. Med.* 325, 1565–1568). In addition, activated protein C (APC) can prevent the lethal effects of *E. coli* in baboon models of gram negative sepsis (Taylor et al., (1987) *J. Clin. Invest.* 79; U.S. Pat. No. 5,009,889 to Taylor and Esmon) and preliminary clinical results suggest that protein C is effective in treating certain forms of human septic shock (Gerson et al., (1993) *Pediatrics* 91, 418–422). These results suggest that protein C may both control coagulation and influence inflammation. Indeed, inhibition of protein S, an important component of the protein C pathway, exacerbates the response of primates to sublethal levels of *E. coli* and augments the appearance of TNF in the circulation (Taylor et al., (1991) *Blood* 78, 357–363). The mechanisms involved in controlling the inflammatory response remain unknown.

Protein C is activated when thrombin, the terminal enzyme of the coagulation system, binds to an endothelial cell surface protein, thrombomodulin (Esmon, (1989) *J. Biol. Chem.* 264, 4743–4746; Dittman and Majerus, (1990) *Blood* 75, 329–336; Dittman, (1991) *Trends Cardiovasc. Med.* 1, 331–336). In cell culture, thrombomodulin transcription is blocked by exposure of endothelial cells to tumor necrosis factor (TNF) (Conway and Rosenberg, (1988) *Mol. Cell. Biol.* 8, 5588–5592) and thrombomodulin activity and antigen are subsequently internalized and degraded (Lentz et al., (1991) *Blood* 77, 543–550, Moore, K. L., et.al., (1989) *Blood* 73, 159–165). In addition, C4bBP, a regulatory protein of the complement system, binds protein S to form a complex that is functionally inactive in supporting APC anticoagulant activity in vitro (Dahlbäck, (1986) *J. Biol. Chem.* 261, 12022–12027) and in vivo (Taylor, et al., 1991). Furthermore, C4bBP behaves as an acute phase reactant (Dahlbäck, (1991) *Thromb. Haemostas.* 66, 49–61). Thus, proteins of this pathway not only appear to regulate inflammation, but they also interact with components that regulate inflammation, and they themselves are subject to down regulation by inflammatory mediators.

It is therefore an object of the present invention to provide a modified protein C which is useful as an improved anticoagulant.

It is a further object of the present invention to provide a method for treating patients with deficiencies in protein C and/or S.

It is another object of the present invention to provide methods of modulating the inflammatory response involving protein C and activated protein C.

SUMMARY OF THE INVENTION

Modified Protein C molecules have been made which substitute the gamma carboxylglutamic acid (Gla) region of another Vitamin K dependent protein, most preferably prothrombin, for the native region of the Protein C. The modified or chimeric protein C has advantages over the wild-type protein C since it is less sensitive to inhibition by natural inhibitors of protein C (which would otherwise decrease the ability of the protein C to act as an anticoagulant) and which do not need the same cofactors or same amounts of cofactors, and can therefore be effective in patients with lowered levels of the cofactors such as protein S or the lipids present in elevated levels in platelets such as phosphatidyl ethanolamine (PE).

As described in the examples, a chimeric protein C was designed after observing that supplementation of phosphatidylserine (PS) containing vesicles with PE enhances activated protein C (APC) anticoagulant activity. To determine the structural basis of the PE sensitivity, a chimeric molecule in which the Gla domain and hydrophobic stack (residues 1–46) of protein C were replaced with the corresponding region of prothrombin (PC-PT Gla) was constructed. The activated chimeric molecule is referred to as APC-PT Gla. APC inactivation of Factor Va was enhanced 10 fold by PE and 2 fold by protein S in either the presence or absence of PE. In purified systems, relative to the chimera, wild type APC inactivated factor Va more rapidly on PE containing vesicles and more slowly on vesicles lacking PE. With APC-PT Gla, inactivation of factor Va was only slightly enhanced by PE and was slightly inhibited by protein S. Prothrombin inhibited inactivation of factor Va by wild type APC much more effectively than the chimera, possibly accounting for the observation that the chimera exhibited approximately 5 fold more plasma anticoagulant activity than wild type APC under all conditions tested. These results demonstrate that the functional influence of PE on factor Va inactivation by APC is mediated by special properties unique to the Gla domain and that the Gla domain of protein C provides specialized functions to greatly enhance interaction with factor Va and protein S on PE containing membranes.

BRIEF DESCRIPTION OF THE DRAWINGS

FIG. 2A graphs the activity of APC and APC-PT Gla at concentrations of between 0 and 5.0 micrograms/ml; FIG. 2B is an expanded view of the activities at concentrations of between 0 and 1.0 micrograms/ml. Wild-type APC in combination with PE, no mAb (closed circles); wild-type APC in combination with PS and anti-protein S mAb (no protein S) (open triangles); wild-type APC in combination with PE and anti-protein S mAb (closed triangles); APC-PT Gla in combination with PE, no mAb (closed upside down triangle); APC-PT Gla in combination with PS, anti-protein S mAb (open diamonds); and APC-PT Gla in combination with PE, and anti-protein S mAb (closed diamonds).

DETAILED DESCRIPTION OF THE INVENTION

Figure 1:
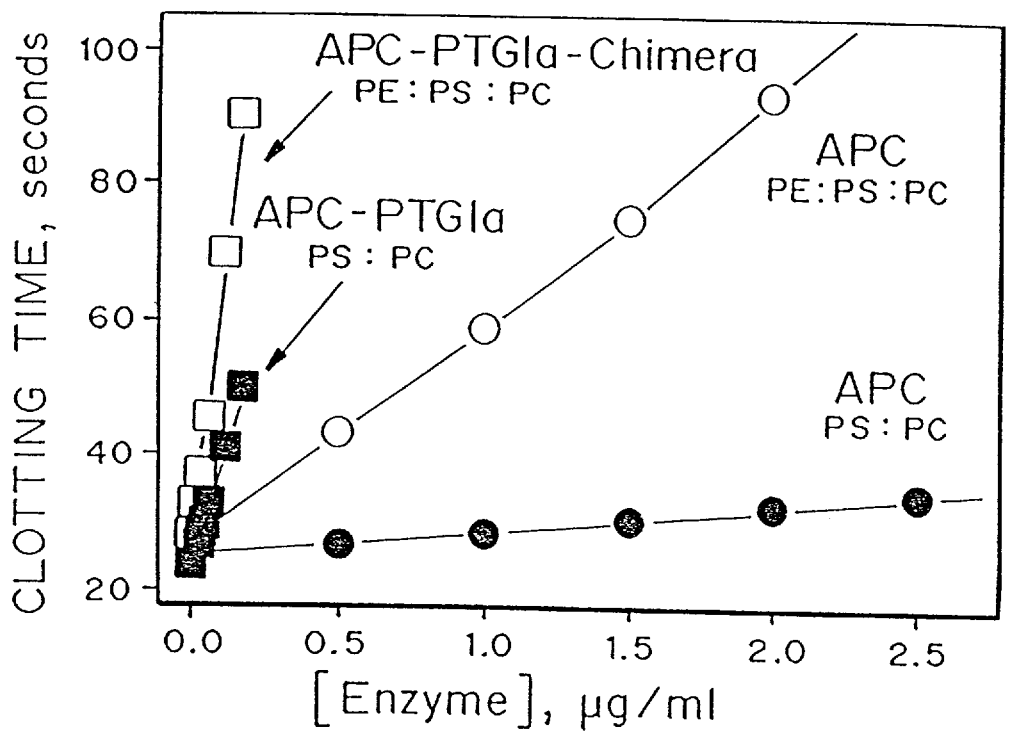
FIG. 1 is a graph showing the anticoagulant activities of APC and APC-PTGla. Clotting time (seconds) is plotted against enzyme concentration (micrograms/ml) for APC-PT Gla in the presence of PE:PS:PC (open squares); APC-PT Gla in the presence of PS:PC (closed blocks); APC in the presence of PE:PS:PC (open circles); and APC in the presence of PS:PC (closed circles).
Figure 2A:
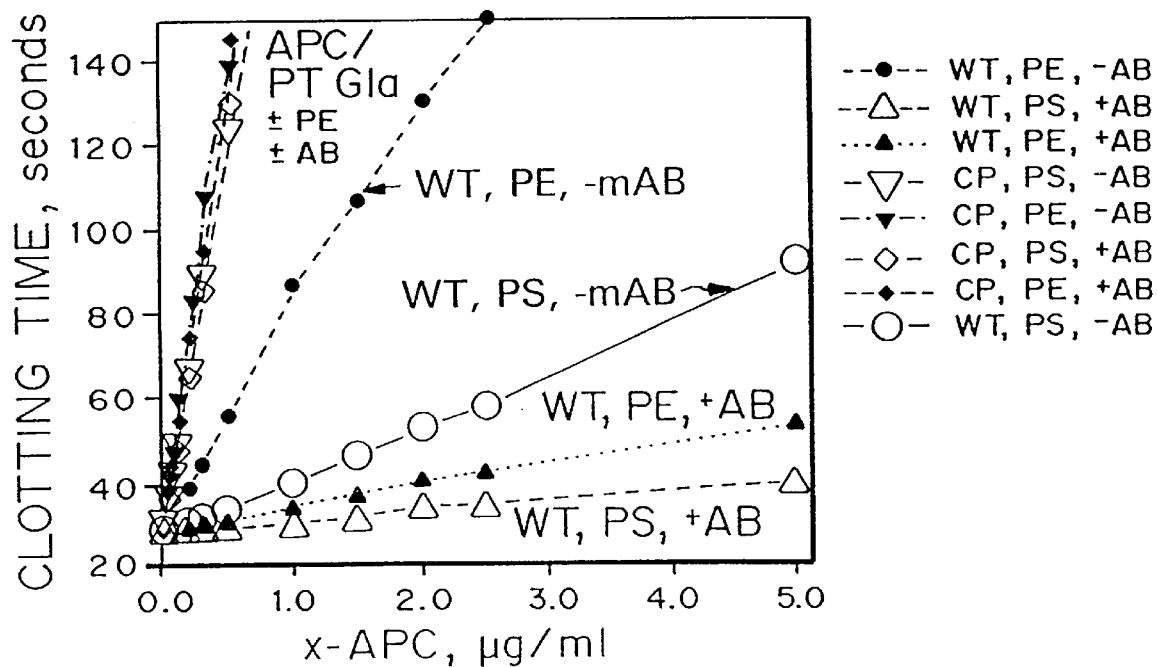
FIGS. 2A and 2B are graphs showing the influence of an antibody to protein S, anti-protein S MAB S155, on the activity of wild-type APC and APC-PT Gla in normal plasma, plotting clotting time (seconds) against concentration of APC or APC-PT Gla (micrograms/ml).
Figure 2B:
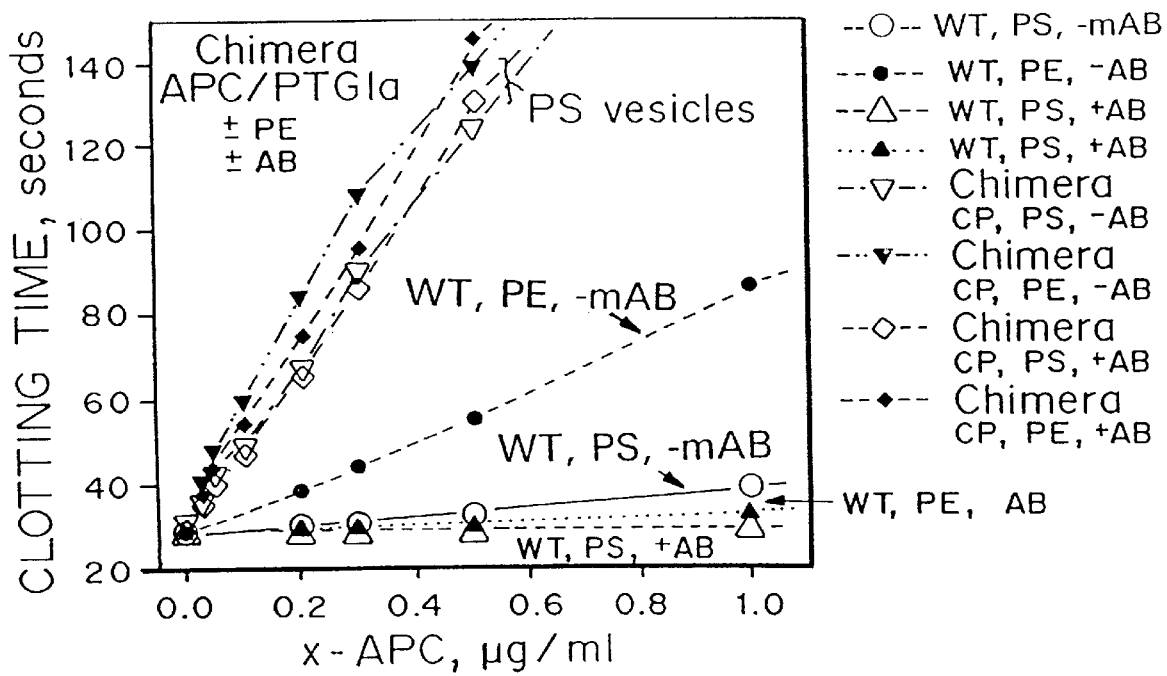
Figure 3A:
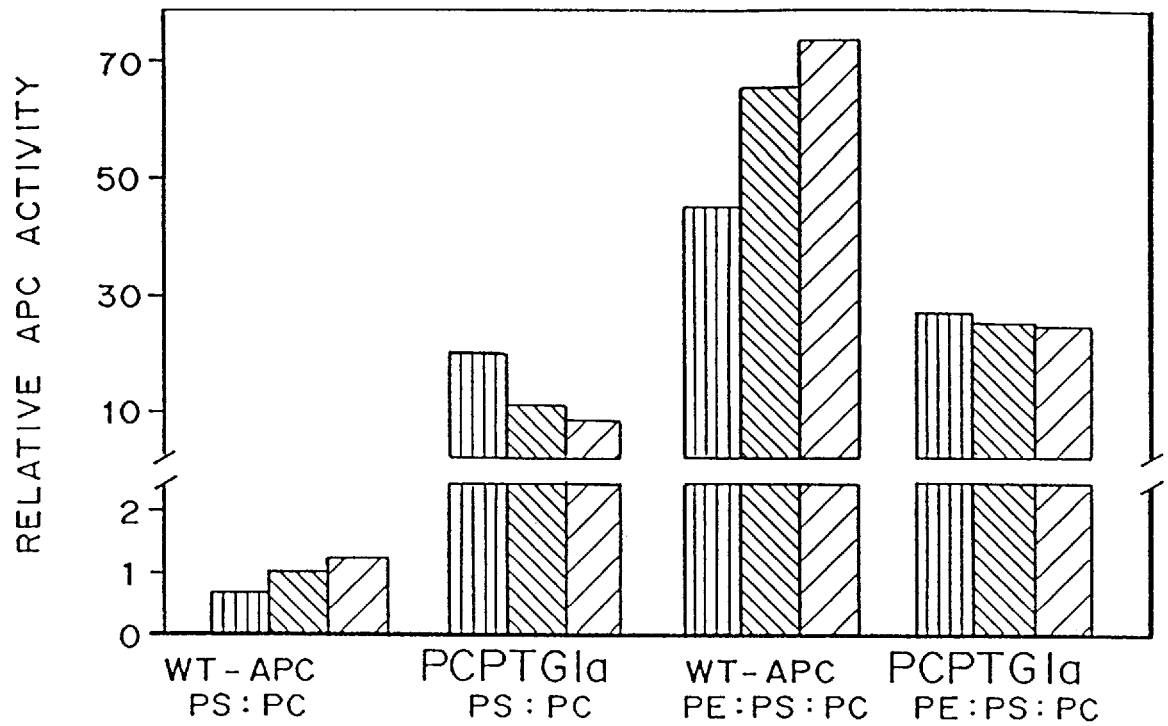
FIGS. 3A and 3B are graphs comparing the relative activity of wild-type APC in combination with PS:PC, PC-PT Gla in combination with PS:PC, wild-type APC in combination with PE:PS:PC, and PC-PT Gla in combination with PE:PS:PC, in the presence (FIG. 3B) and absence (FIG. 3A) of prothrombin at a physiological concentration of 1.4 micromolar. The APC concentration required in the presence of protein S and vesicles without PE is defined as one. Relative activity is calculated as the concentration under standard conditions required to inhibit 50 activity in 30 minutes divided by the concentration under experimental conditions required to inhibit 50% activity in 30 minutes.
Figure 3B:
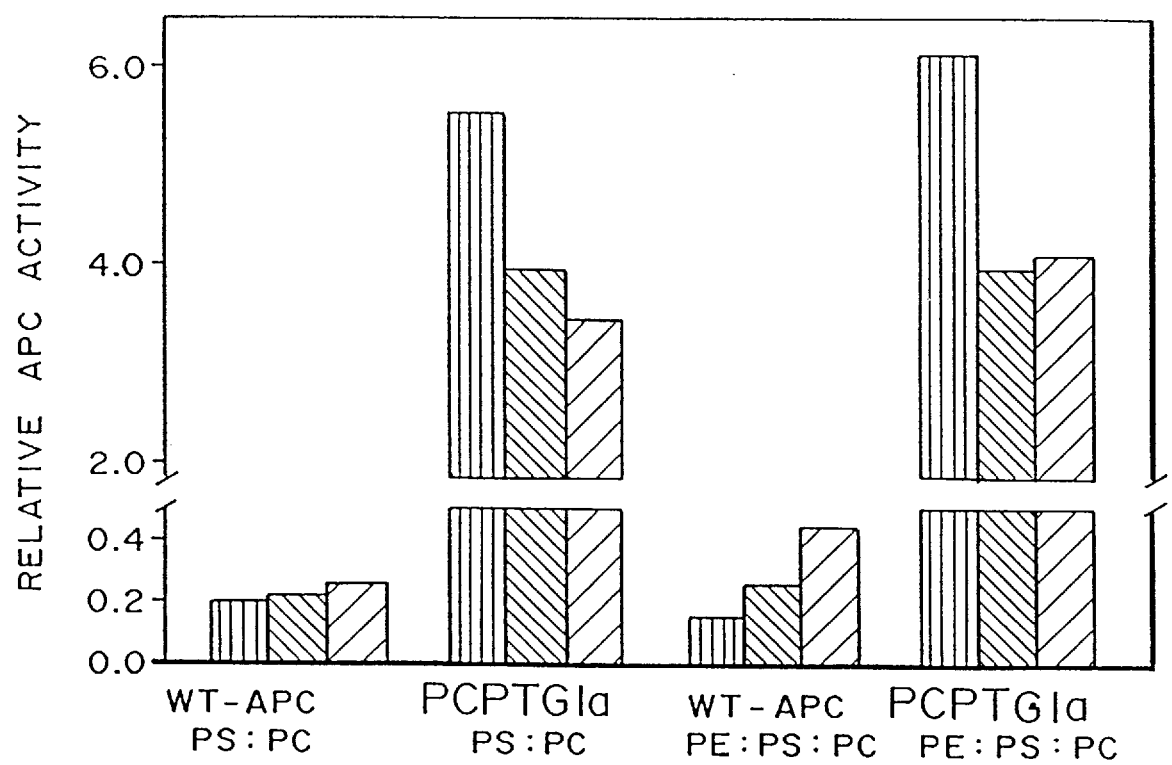

Assembly of multiprotein enzyme complexes on negatively charged phospholipid membrane surfaces is critical to both the formation and regulation of the blood clotting process. Zymogen activations occur rapidly when the enzyme, usually a vitamin K dependent protein, binds to a cofactor, usually a non-vitamin K dependent protein, to activate a substrate, usually a vitamin K dependent protein (reviewed in Mann, et al. (1988) *Ann. Rev. Biochem.* 57, 915–956; Furie and Furie (1988) *Cell* 53, 505–518). The enzymes and substrates interact with the membrane reversibly, while the cofactors may either bind reversibly or be integral membrane proteins. The nature of the phospholipid head group appears to contribute to catalytic and binding efficiency with phosphatidylserine (PS) being generally accepted as the most important phospholipid (Mann, et al. (1988); Pei, et al. (1993) *J. Biol. Chem.* 268, 3226–3233). The vast majority of biophysical and kinetic studies of the assembly of the vitamin K dependent complexes have used membranes composed solely of phosphatidylcholine (PC) and PS (Mann, et al., Pei, et al., Castellino, F. J. (1995) *Trends Cardiovasc. Med.* 55–62; Nelsestuen, (1978) *Biochemistry* 17, 2134–2138).

Recently, it was observed that phosphatidylethanolamine (PE), a major constituent of the outer leaflet of the membrane of activated platelets (Bevers, E. M., Comfurius, P., and Zwaal, R. F. A. (1983) *Biochim. Biophys. Acta* 736, 57–66), plays an important role in the function of one of these complexes, the activated protein C (APC) dependent inactivation of factor Va (Smirnov and Esmon (1994) *J. Biol. Chem.* 269, 816–819). In this case, the presence of PE or cardiolipin potently enhanced the rate of inactivation. Subsequently, roles for PE in factor VIII binding (Gilbert and Arena (1995) *J. Biol. Chem.* 270, 18500–18505), tissue factor-factor VIIa activation of factor X (Neuenschwander, et al. (1995) *Biochemistry* 34, 13988–13993) and prothrombin activation (Billy, et al. (1995) *J. Biol. Chem.* 270, 26883–26889; Smeets, et al. (1996) *Thromb. Res.* 81, 419–426) have been reported. In the case of prothrombin activation, with PE present, the amount of PS required to support prothrombin activation was reduced several fold. In the case of tissue factor, it was shown that the presence of PE enhanced activation primarily by decreasing the amount of PS required for optimal activation and this was largely a Km effect on the substrate. The impact of PE on the inactivation of factor Va was substantially greater than on the other systems. For prothrombin activation and tissue factor mediated factor X activation, the augmentation by PE could be overcome simply by increasing PS concentration whereas the PE impact on factor Va inactivation was not eliminated by high PS (Smirnov 1994).

Protein C, like the other vitamin K dependent proteins, is composed of several domains (Furie 1988). These include the protease domain, two EGF like domains, an aromatic stack and the vitamin K dependent Gla domain containing the 4-carboxyglutamic acid (Gla) residues. These Gla residues are involved in $Ca^{2+}$ dependent membrane binding and are clustered within the amino terminal 48 residues of the vitamin K dependent plasma factors (Furie 1988, Castellino 19954, Mann, K. G., Krishnaswamy, S., and Lawson, J. H. (1992) *Sem. Hematol.* 29, 213–226). The sequences of these proteins within this region are highly conserved, but the number of Gla residues varies from 9 to 12 (Furie 1988). Since the Gla domains are implicated in the membrane binding and membrane dependent catalytic activity, it was postulated that the differences in PE dependent behavior between protein C and the other complexes might be mediated by the Gla domains. To test this possibility, a chimeric form of protein C in which the Gla domain has been exchanged with that of prothrombin was designed in an effort to evaluate the regions of the molecules involved in the PE dependent activities.

The chimera was designed to be non-immunogenic in humans, as well as to have the advantageous properties demonstrated in the examples. Exons one to three of protein C were replaced with exons one to three of prothrombin. This region includes the signal peptide, the Gla domain and the aromatic stack region. The splice sites in both the protein C and the prothrombin are identical, so that no sequence changes were required and only human sequence present in the naturally occurring human proteins is present in the chimeras. The activation site in the protein C zymogen was unaffected by the change.

The results of the studies reported below show that the substitution of the native Gla domain with the prothrombin Gla domain alters the activity of the protein C, decreasing the need for PE and protein S and reducing inhibition by prothrombin. The PE dependence of APC anticoagulant activity is clearly mediated in large part by the Gla domain of protein C. APC-PT Gla exhibited little dependence on the presence of PE in the liposomes in purified systems. Furthermore, the factor Va inactivating activity of the chimera was inhibited rather than stimulated by protein S. These differences were not due to defects in membrane binding since the chimera bound to membranes at least as well as wild type protein C and was more active than wild type of vesicles devoid of PE while being less active on vesicles containing PE. Much of this difference appears to lie in the capacity of protein S and factor Va to synergistically augment APC binding to vesicles, especially those containing PE. In particular, in the presence of factor Va, protein S failed to enhance binding of the chimera as it did in the case of wild type APC.

In plasma, the chimera exhibited much greater anticoagulant activity than wild type APC on vesicles with or without PE. These differences appeared to be due, in part, to the decreased ability of prothrombin to block factor Va inactivation by the chimera.

The PE effects on catalysis of the APC anticoagulant complexes have both a cell biology and pathophysiology ramification. PE has been reported to be present on the surface of unactivated cells (Wang, et al. (1986) *Biochem. Biophys. Acta* 856, 244–258) and, following activation, may constitute nearly 40% of the outerleaflet membrane phospholipid (Bevers, et al. 1983). Furthermore, PE has been reported to have a higher Km for the flipase and hence is likely to be more slowly transported to the inner membrane leaflet (Devaux (1991) *Biochemistry* 30, 1163–1173). Therefore, if the different coagulation complexes were to exhibit widely different PE:PS dependencies, this time dependent change in membrane composition could selectively favor clot promoting or clot inhibiting reactions.

Although demonstrated by the substitution of the Gla region of the protein C with the Gla region of prothrombin, many of the other Vitamin K dependent clotting factors are equally well understood and their Gla regions could be inserted in place of the N-terminal regions of protein C to create a chimera having altered anticoagulant activity. Unlike some systems, the coagulation system is highly predictable based on in vitro results and the highly conserved structure within the clotting proteins provides a means for extrapolation among proteins. Other representative donor proteins include factor X and factor VII. The chimeras are made using the same techniques described in detail in the example. The DNA encoding the other Vitamin K dependent clotting factors is known and described in the literature.

Pharmaceutical Compositions

The protein is generally effective when administered parenterally in amounts above about 90 µg/kg of body weight, assuming 35 ml plasma/kg, approximately three to four micrograms protein C/ml plasma, and one to three micrograms chimeric protein C/ml plasma. Based on extrapolation from other proteins, for treatment of most inflammatory disorders, the dosage range will be between 20 and 200 micrograms/kg of body weight.

The modified protein C is preferably administered in a pharmaceutically acceptable vehicle. Suitable pharmaceutical vehicles are known to those skilled in the art. For parenteral administration, the compound will usually be dissolved or suspended in sterile water or saline.

Disorders to be Treated

It should be possible to treat disorders where protein S is low, some forms of lupus, following stroke or myocardial infarction, after venous thrombosis and in disseminated intravascular coagulation, septic shock, adult respiratory distress syndrome, and pulmonary emboli using the modified protein C. Protein S levels are often low in these conditions, making APC less effective as an anticoagulant (see D'angelo, et al. (1988) *J. Clin. Invest.* 81, 1445–1454). Examples of these conditions include disseminated intravascular coagulation, during warfarin anticoagulation, and in thromboembolic disease. Since the chimera's optimal activity does not depend on normal levels of protein S in the patient, it is expected to be an active anticoagulant in conditions where the patient's own activated protein C or therapeutically administered protein C or activated protein C would be compromised. Note that for technical reasons, protein S concentrates useful for treatment have not been successfully prepared.

Lupus anticoagulants and some antiphospholipid antibodies block the function of coagulation and anticoagulation complexes preferentially on PE containing membranes (Smirnov, et al. (1995) *J. Clin. Invest.* 95, 309–316; Rauch, et al. (1986) *J. Biol. Chem.* 261, 9672–9677). These antibodies are associated with an increased risk of thrombosis (Ginsberg, et al. (1993) *Blood* 81, 2958–2963; Triplett, D. A. (1993) *Arch. Pathol. Lab. Med.* 117, 78–88; Pierangeli, et al. (1994) *Thromb Haemostas.* 71, 670–674). In addition to therapeutic applications, the APC molecule with no PE dependence allows the exploration of the mechanisms of PE dependent lupus anticoagulant effects on the APC system in vitro and in vivo. The chimera is less sensitive to inhibition by lupus anticoagulants and hence can be used to identify pathogenic antibody populations that react with protein C.

The present invention will be more fully understood by reference to the following non-limiting examples. The following abbreviations are used herein: APC, activated protein C; PC-PT Gla, a chimeric molecule in which the Gla domain and hydrophobic stack (residues 1–45) of protein C has been replaced with the corresponding region of prothrombin; PE, phosphatidylethanolamine; PS, phosphatidylserine; PC, phosphatidylcholine; Gla, 4-carboxyglutamic acid; X-CP, the factor X activator from Russell's viper venom; BSA, bovine serum albumin; TBS, 150 mM NaCl, 20 mM Tris-HCl, 0.02% sodium azide, pH 7.4; TBS-GOB, TBS containing 1 mg/ml gelatin, 1.6 mg/ml ovalbumin and 10 mg/ml BSA.

EXAMPLE 1

Construction of a Chimeric Protein C-Prothrombin Protein

Experimental Procedures

Proteins and reagents. Human thrombin and prothrombin (Owen, et al. (1974) *J. Biol. Chem.* 249, 594–605), human APC (Esmon, et al. (1993) *Meths. Enzymol.* 222, 359–385), human protein S (Taylor, et al. (1991) *Blood* 78, 356–363), human factor Xa (Le Bonniec, et al. (1994) *J. Biol. Chem.* 267, 6970–6976), bovine factor Va (Esmon, C. T. (1979) *J. Biol. Chem.* 254, 964–973), and the factor X activator from Russell's viper venom (X-CP)(Esmon, C. T. (1973) (Ph.D. Dissertation), Washington University, St. Louis) were prepared as described. Meizothrombin labeled in the active site with fluorescein was prepared as described by Armstrong, et al. (1990) *J. Biol. Chem.* 265, 6210–6218; Bock (1988) *Biochemistry* 27, 6633–6639. Human factor Va was obtained from Hematologic Technologies. Bovine serum albumin (BSA), Russell's viper venom, ovalbumin, gelatin, MOPS, Tris-HCl and salts were obtained from Sigma. The chromogenic substrates Spectrozyme TH and Spectrozyme PCa were obtained from American Diagnostica (Greenwich, Conn.). The irreversible inhibitor of the serine proteases (p-amidinophenyl)methanesulphonyl fluoride was obtained from Calbiochem. 1-palmitoyl-2-oleoyl-sn-glycero-3 PS, 1-palmitoyl-2-oleoyl-sn-glycero-3 PC and 1,2-dilinoleoyl-sn-glycero-3-PE were obtained from Avanti Polar Lipids Inc. 1-Palmitoyl-2- [1-$^{14}$C-oleoyl]PC was obtained from DuPont NEN. Factor V deficient human plasma was obtained from George King Bio-Medical, Inc. (Overland Park).

Preparation of Phospholipid Vesicles.

Sonicated vesicles were prepared as described (Smirnov 1994). Briefly, lipids were mixed in the weight proportions described below, dried under argon and lyophilized overnight to remove organic solvents. They were then reconstituted in 150 mM NaCl, 20 mM Tris-HCl, 0.02%, sodium azide, pH 7.4 (TBS) to 2 mg total lipid/ml and sonicated (Bronson Sonic Power Co, model 350) 15 min in an ice-water bath under argon flow, centrifuged at 8000 g for 15 min and filtered through a 0.22 µm filter. The vesicles were used immediately or stored at +20° C. Storage did not alter vesicle activity.

Construction of the Protein C Prothrombin Gla Domain Chimera.

The protein C chimera was constructed in which the first 3 exons of prothrombin (i.e. coding for the signal peptide, the Gla domain and the aromatic stack regions) replaced the corresponding regions of protein C.

The relevant amino acid sequences for human prothrombin and protein C are: human prothrombin (Sequence ID No. 1): A N T F L x x V R K G N L x R x C V x x T C S Y x x - AFxALxSSTATDVFWA human protein C (Sequence ID No. 2): ANSFLxxLRHSSLxRxCIxxICDFxx-AKxIFQNVDDTLAFWS where x means gamma carboxylglutamic acid.

Mutagenesis was performed by polymerase chain reaction methodology. The wild type protein C cDNA (provided by Eli Lilly Research Laboratory) was ligated into the HindIII and XbaI sites of pRc/RSV (Invitrogen, Calif.) to form RSV-PC as described by Rezaie 1993. There is a unique BstEII restriction site in the protein C cDNA in the beginning of exon 4, which encodes the N-terminal EGF domain. Double digestion of RSV-PC with HindIII and BstEII removes the DNA sequences of the first 3 exons of protein C as well as the first codon of exon 4, which is an Asp. To exchange exons 1–3 of protein C with those of prothrombin, two PCR primers were synthesized. The forward prothrombin sense primer 5'-CGCTAAGCTTCCATGGCCCGCATCCGAGGCTT-3' (Sequence ID No. 3) starts from the initiation codon of the prothrombin cDNA (provided by Dr. Ross MacGillivray) and contains a HindIII restriction enzyme site at the 5'-end of the primer (underlined). The reverse prothrombin antisense primer 5'-GAGTGGTCACCGTCTGTGTACTTGGCCCAGAA-CA-3' (Sequence ID No. 4) starts from the nucleotide of exon 3 in the prothrombin cDNA and contains the native BstEII restriction enzyme site containing the missing Asp codon in the beginning of exon 4 of the protein C cDNA.

Following PCR amplification of prothrombin cDNA with these two primers and double digestion with HindIII and BstEII, the DNA fragment was ligated into the identical sites of the wild type protein C expression vector described above.

After sequencing, the mutant construction was transfected into human 293 cells and the chimeric protein C was purified from culture supernatants by immunoaffinity chromatography using the calcium dependent monoclonal antibody, HPC4, as described by Rezaie and Esmon (1993) *J. Biol. Chem.* 268, 19943–19948, Rezaie, A. R. and Esmon, C. T. (1992) *J. Biol. Chem.* 267, 26104–26109). The PC-PT Gla chimera was activated to form APC-PT Gla by thrombin in the presence of 2 mM EDTA and purified by Mono-Q FPLC chromatography (Pharmacia) essentially as described for wild type protein C by Esmon, C. T., et al., Methods. Enzymol. 222, 259–385 (1993).

Gla residue determinations were performed by Dr. Betty Yan and Cindy Payne at Eli Lilly Research Laboratory. The Gla content per mole protein obtained were: 8.7±0.3 for protein C, 10.9±0.2 for prothombin, 9.5±0.2 for PC-PT Gla and 10.3±0.4 for APC-PT Gla.

EXAMPLE 2

Determination of Protein C and Prothrombinase Activity of Chimeric Protein

Methods and Materials

Measurement of APC and Prothrombinase Activity in the Purified System.

Factor Va inactivation was analyzed with a three stage assay essentially as described by Smirnov and Esmon (1994). Briefly, factor Va was inactivated by APC in the first stage. In the second stage, after inactivation of APC with (p-amidinophenyl)methanesulphonyl fluoride, residual factor Va activity was monitored by its activity in the prothrombinase complex in the presence of excess factor Xa and prothrombin. The resultant thrombin was measured in the third stage using a chromogenic assay. All reagents were diluted in TBS containing 1 mg/ml gelatin, 1 mg/ml and 10 mg/ml BSA (TBS-GOB). Percent factor Va inactivation was calculated by dividing thrombin formation in the presence of APC by thrombin formation in its absence and subtracting this value from 1.

Enzyme was added at concentration of 0.002, 0.005, 0.01, 0.02, 0.05, 0.1, 0.15, 1 and 4 ng/ml. When held constant, the final concentration of reagents were 0.2 nM factor Va, 1 nM factor Xa, 1.4 μM prothrombin and 10 μg/ml phospholipid.

Clotting Assays.

Clotting assays were performed by a modification of the dilute Russell's viper venom test. Purified X-CP was employed instead of crude venom. All reagents were diluted in TBS containing 1 mg/ml gelatin. Assays were performed in 96-well plates. To serial dilutions of APC (30 μl) were added 10 μl of 60 μg/ml phospholipid, 10 μl of 20 ng/ml X-CP and 10 μl of normal pooled plasma. The entire mixture was incubated for 1 min. Clotting was initiated by addition of 25 μl of 20 mM $CaCl_2$. The clotting time was determined on a Vmax Kinetic Microplate Reader.

Adsorption of Liposomes onto Latex.

A 10% suspension of latex beads (50 μl) was pelleted in Eppendorf tubes and washed 3 times with PBS by centrifugation at 8,000×g for 1 min and resuspended in 50 μl TBS, 5 mM $CaCl_2$. Liposomes (100 μl at 1 mg/ml total phospholipid in TBS) were added and incubated 2 hr at 37° C. with shaking. After two washes, the beads were resuspended in TBS-GOB and further incubated 2 hr at room temperature with shaking. After 2 additional washes with TBS, the beads were resuspended in 500 μl TBS. Total phospholipid concentration was determined by counting the $^{14}$C-PC tracer included in the phospholipid mixtures (Beckman Model LS 6000SE scintillation counter) and found to be 50 μg/ml of latex suspension for both PS:PC and PE:PS:PC adsorbed liposomes. The beads could be stored at 4° C. for at least 7 days without loss of adsorbed phospholipid.

Fluorescent Labelling.

Active site fluorescein labeled enzymes were prepared according to the method of Bock (1988). Briefly, to 300 μl of enzyme (1 mg/ml) were added 40 μl 1M HEPES, pH 7.4, 1 μl 0.2M EDTA and two times 5 μl of N-$^{\alpha}$[(acetylthio) acetyl]-D-Phe-Pro-Arg-$CH_2Cl$ (4 mM), 10 min per incubation, to form ATA-FPR-enzyme. After overnight dialysis, 45 μl hydroxylamine (1M in 1M HEPES, pH 7.4) and 50 μl of 5-(iodoacetamido)fluorescein (Molecular probes, 1 mg/ml in 1M HEPES, pH 7.4) were added to the ATA-FPR-enzymes and incubated 1 h at 0° C. Free fluorescein was removed by gel filtration on a PD-10 column (Pharmacia), and the samples were then dialyzed overnight at 4° C. With this method, each molecule of labelled enzyme contains a single dye at the same location and thus, all of the fluorescent molecules behave equivalently.

Binding of Fluorescein Labelled Proteins to Liposomes Adsorbed on Latex.

Liposome adsorbed latex beads (0.5 μg total phospholipid/ml) were suspended in TBS-GOB containing 2.5 mM $CaCl_2$. Appropriate protein(s) were added at the concentrations indicated and incubated at 25° C. for 20 min in the dark with occasional mixing. Binding was analyzed on a FACScan flow cytometer (Becton Dickinson). To determine the calcium independent, irreversible component of the fluorescent APC binding, 50 mM EDTA was added in 200 mM MOPS, pH 7.4 to a final concentration of 10 mM, and samples were re-analyzed after 20 min incubation in the dark. This component accounted for less than 20% of the observed binding. Binding parameters were determined by fitting the calcium dependent binding to the equation for single site binding model using the ENZFITTER™ program (Elsevier Biosoft, Cambridge, UK).

Liposome-Protein Interactions Measured by Right Angle Light Scattering.

Right angle light scattering was performed as described by Nelsestuen (1978) and Castellino (Zhang and Castellino 1993) on an SLM 8000 fluorimeter (SLM Instruments, Urbana, Ill.) with the wavelength set at 320 nm. The liposome concentration was 50 $\mu$g/ml. Binding experiments were performed in TBS, pH 7.4 containing 5 mM $CaCl_2$. The prothrombin and protein C concentrations were varied from 0 to 3 $\mu$M, and the PC-PT Gla concentrations were varied from 0 to 1.2 $\mu$M. Binding parameters were determined by fitting the reversible calcium dependent binding to the equation for single-site binding model using the ENZFITTER program.

Results

PC-PT Gla could be activated to form an enzyme with amidolytic activity toward Spectrozyme PCa equivalent to wild type APC. The concentration dependence of inactivation of factor Va between APC and the APC chimera on vesicles with or without PE supplementation was then compared. On vesicles composed solely of PS:PC, the chimera was approximately 5 times more active than wild type APC. PE enhanced factor Va inactivation by the chimera very little (about 1.6 fold in this experiment) compared to approximately a 15 fold enhancement of APC. In addition, protein S (2.5 $\mu$g/ml protein S) inhibited factor Va inactivation by the chimera whereas protein S enhanced factor Va inactivation by APC. These effects were not PE dependent. Therefore, it appears that much of the PE dependence of APC is mediated by the Gla domain and that some portion of the Gla domain is important for protein S mediated effects in purified systems.

To ascertain whether the differences in activity were reflected in differences in binding affinity to membranes, light scattering experiments were initially performed with prothrombin, protein C and PC-PT Gla on PS:PC vesicles containing either 20 or 50% PS. Prothrombin, protein C and PC-PT Gla were bound to liposomes (20%PS:80%PC liposomes) (50 $\mu$g/ml) in TES, pH 7.4 containing 5 mM $CaCl_2$. Protein binding was measured by right angle light scattering.

It was apparent that the amount of prothrombin bound to the vesicles containing 20% PS was much higher than the amount of protein C bound with the PC-PT Gla being somewhat greater than the protein C. The Kd values were similar for all proteins. Increasing the PS concentration to 50% increased the amount of protein C and chimera binding more than two fold, but had a relatively small effect on prothrombin binding. From these experiments it is apparent that the PC-PT Gla binds to membranes at least as well protein C, but the affinity is not significantly better than wild type and hence cannot account for the increased activity on PS vesicles. The differences in maximum binding between the protein C and prothrombin presumably reflects the maximum number of molecules bound per liposome and the approximately 20% larger molecular mass of prothrombin.

It was possible that the differences in activity between wild type and the chimera reflect differences in interaction with other protein components, and therefore light scattering approaches could not be employed easily. Furthermore, PE containing vesicles are too large to utilize in light scattering approaches. Therefore, different binding methodologies had to be employed that would allow the presence of PE and/or other protein components. This was accomplished by flow cytometry. Liposomes adsorbed to latex were employed and binding was monitored as a function of increasing fluorescent enzyme concentration. The final concentration of phospholipid was 0.5 $\mu$g/ml, and, when present, protein S (pro S) was 100 nM and factor Va (FVa) was 10 nM. All flow cytometric measurements were done with the enzymes labeled in the active site with fluorescein. All light scattering experiments were performed with the zymogens except the meizothrombin experiments in which the enzyme activity was blocked with D-Phe-Pro-Arg chloromethylketone as described by Armstrong, et al. (1990). On PS:PC vesicles, the concentration dependence of binding of protein C by light scattering and the concentration dependence of APC binding to latex adsorbed vesicles was indistinguishable, thereby validating this approach. The data from the light scattering measurements and the flow cytometric analysis was plotted as a function of increasing protein concentration. The curves were overlayed after normalizing the curves to the maximum binding calculated with the Enzfitter program assuming a single class of binding sites. The Kd values for prothrombin and meizothrombin were also similar as determined by light scattering, and the meizothrombin binding was equivalent by the two methods, further validating this approach.

The major feature distinguishing wild type and APC-PT Gla is the degree to which protein S and factor Va synergize to augment membrane binding. Comparison of the chimera and wild type APC reveals that the binding affinity of wild type APC is higher than that of the chimera on PE containing vesicles when both factor Va and protein S are present and weaker when binding is examined on phospholipid devoid of PE. Factor Va alone and protein S alone had relatively little influence on the binding affinity of wild type APC, but factor Va alone enhanced chimera binding to a greater extent than wild type, especially in the absence of PE.

Their ability to anticoagulate plasma was then studied to determine whether these differences in properties between APC and the chimera were retained under more physiological conditions. Surprisingly, the chimera exhibited much higher anticoagulant activity than APC on vesicles with or without PE. Unlike the situation with purified proteins, in plasma the chimera was much more active than wild type APC on PE containing vesicles.

The much greater anticoagulant activity of the chimera in plasma could be due either to producing interactions specific to the chimera or, more likely, resistance to inhibitory factors. One possible inhibitor is prothrombin which circulates at very high concentrations. In principal, prothrombin could interfere with APC more effectively than with the chimera. To test this possibility, and the potential effect of protein S on this interaction, factor Va inactivation was analyzed as follows: Inactivation of factor Va by APC occurring in 30 minutes in the presence of 2.5 $\mu$g/ml protein S on PS:PC vesicles was defined as the standard condition. The concentration of APC required to inactivate 50% of the factor Va under the standard conditions was assigned a relative activity of 1. The concentration of APC or chimera required to inhibit 50% of the factor Va under various experimental conditions (±prothrombin, ±protein S, ±PE in the vesicles) in the first stage of the assay was then determined. This value was divided into the APC concentration determined for the standard condition to determine the relative activity.

Factor Va inactivation was performed as usual with the exception that 1.4 $\mu$M prothrombin was present in the first stage of the assays. Three concentrations of protein S: 0, 2.5 $\mu$g/ml, and 5 $\mu$g/ml were employed. Lipids were either PS:PC or PE:PS:PC. The relative activity was calculated as described above. Comparison of factor Va inactivation in the absence and the presence of prothrombin indicated that prothrombin inhibited APC inactivation of factor Va on either type of vesicle and independent of the presence of protein S. Prothrombin inhibited factor Va inactivation 5 fold in the absence of PE and nearly 100 fold in the presence of PE. In contrast, the chimera was much less sensitive to prothrombin, with inhibition of about 5 fold observed in the presence or absence of PE. This decreased sensitivity to prothrombin inhibition may account in part for the enhanced plasma anticoagulant activity of the chimera.

EXAMPLE 3

Use of Chimeric Protein as a Research Reagent

In plasma, protein S plays additional roles in the anticoagulant activity of APC. For instance, previous studies have shown that protein S can block the ability of factor Xa to protect factor Va (Solymoss, et al. (1988) *J. Biol. Chem.* 263, 14884–14890) from inactivation and that protein S can interfere directly with the assembly of the prothrombinase complex (Heeb, et al. (1993) *J. Biol. Chem.* 268, 2872–2877).

To test the possibility that one or more of these influences of protein S were observed with the chimera on PE containing vesicles, protein S was blocked with an inhibitory monoclonal antibody and the anticoagulant activities of activated protein C and the chimera were examined in plasma. Plasma clotting was performed under standard conditions in the presence and absence of an inhibitory monoclonal antibody to protein S (300 μg/ml of the protein S inhibitory monoclonal antibody S155 present in the final clotting mixture).

In plasma, the anticoagulant activity of the chimera remained relatively insensitive to protein S (i.e., the anticoagulant activity was not affected by antibody on vesicles devoid of PE (20%PS:80%PC liposomes) and only slightly reduced on vesicles containing PE (50%PE:20%PS:30%PC liposomes)). The anticoagulant activities of APC and the chimera were examined for Protein S dependence. Thus, protein S functions in plasma appear to be largely dependent on specific properties contributed by the protein C Gla domain.

The teachings of the references cited herein are specifically incorporated herein. Modifications and variations of the present invention will be obvious to those skilled in the art from the foregoing detailed description and are intended to be encompassed by the following claims.

We claim:

1. A nucleic acid molecule encoding a protein C chimeric protein wherein the gamma carboxylglutamic acid region of the protein C has been replaced with the gamma carboxylglutamic acid region of prothrombin.

2. The nucleic acid molecule of claim 1 wherein the protein C and the prothrombin are human proteins.

3. The nucleic acid molecule of claim 1 wherein the first three exons encoding protein C are replaced with the first three exons encoding prothrombin.

4. A method of making a nucleic acid molecule encoding a protein C chimeric protein wherein the gamma carboxylglutamic acid region of the protein C has been replaced with the gamma carboxylglutamic acid region of prothrombin comprising preparing a first nucleic acid sequence by excising the nucleic acid sequence encoding the gamma carboxyl-glutamic acid region from a nucleic acid sequence encoding protein C, preparing a second nucleic acid sequence by excising the nucleic acid sequence encoding the gamma carboxyl-glutamic acid region from a nucleic acid sequence encoding prothrombin, and linking the two sequences together to form a cassette encoding a chimeric protein C protein.

5. The method of claim 4 wherein the protein C and the prothrombin are human proteins.

6. The method of claim 4 wherein the first three exons encoding protein C are replaced with the first three exons encoding prothrombin.

7. The method of claim 4 further comprising the step of inserting the cassette into an expression vector and expressing the protein.

* * * * *